United States Patent [19]

Gasparro et al.

[11] Patent Number: 5,256,648
[45] Date of Patent: Oct. 26, 1993

[54] SELECTIVE INHIBITION OF GENE EXPRESSION BY PHOTOACTIVATABLE OLIGONUCLEOTIDES

[75] Inventors: Francis P. Gasparro, Hamden; Richard L. Edelson, Westport, both of Conn.

[73] Assignee: Yale University, New Haven, Conn.

[21] Appl. No.: 410,622

[22] Filed: Sep. 21, 1989

Related U.S. Application Data

[63] Continuation-in-part of Ser. No. 299,265, Jan. 23, 1989, abandoned, which is a continuation-in-part of Ser. No. 146,571, Jan. 21, 1988, abandoned.

[51] Int. Cl.$^5$ .................. C12N 15/00; C07H 21/04
[52] U.S. Cl. .................. 514/44; 435/172.3; 536/24.5; 514/455
[58] Field of Search .................. 514/44; 435/172.3; 536/27

[56] References Cited

U.S. PATENT DOCUMENTS 5,112,963   5/1992   Pieles et al.

OTHER PUBLICATIONS

Nucleic Acids Research, 15:6843–6854, Sep. 1987, Shi et al., The Effects of Covalent Additions of a Psoralen on Transcription by *E. coli* RNA Polymerase.
Nucleic Acids Research, 15:5749–5763, Jul. 1987, Marcus-Sekura et al., Comparative Inhibition of Chloramphenicol Acetyltransferase Gene Expression by Antisense Oligonucleotide Analogues Having Alkyl . . . .
Cell, 45:567–574, May 23, 1986, Courey et al., The Use of Psoralen-Modified DNA to Probe the Mechanism of Enhancer Action.
PNAS, 84:648–652, Feb. 1987, Le Maitre et al., Specific Antiviral Activity of a Poly(L-lysine)-conjugated Oligodeoxyribonucleotide Sequence Complementary to . . . .
Science, vol. 241, issued Aug. 12, 1988 (K. Yamasaki et al.), "Cloning and Expression of the Human Interleukin-6 (BSF-2/IFN Beta 2) Receptor", pp. 825–828.
Biological Abstracts, vol. 81, issued Feb. 1, 1986, Stanley et al., "The Structure and Expression of the Murine Gene Encoding Granulocyte-Macrophage Colony Stimulating Factor: Evidence for Utilization of Alternative Promoters".
Proceedings of the National Academy of Sciences, U.S.A., vol. 84, issued Dec. 1987, L. H. Martin et al., "Structure and Expression of the Human Thymocyte Antigens CD1a, CD1b, and CD1c", pp. 9189–9193.
Nucleic Acids Research, vol. 14, issued Apr. 25, 1986, Y. Furutani et al., "Complete Nucleotide Sequence of the Gene of Human Interleukin 1 Alpha", pp. 3167–3179.
Nucleic Acids Research, vol. 17, issued Jul. 25, 1989, C. M. Ballantyne et al., "The Nucleotide Sequence of the cDNA for Murine Intercellular Adhesion Molecule-1 (ICAM-1)", p. 5853.
The EMBO Journal, vol. 6, issued Apr. 1987, S. K. A. Law et al., "The Primary Structure of the Beta-subunit of the Cell Surface Adhesion Glycoproteins LFA-1, CR3 and p150,95 and Its Relationship to the Fibronectin Receptor", pp. 915–919.

*Primary Examiner*—Robert J. Hill, Jr.
*Assistant Examiner*—John D. Ulm
*Attorney, Agent, or Firm*—Kenyon & Kenyon

[57] ABSTRACT

A method of inhibiting the function of targeted DNA in a viable cell comprising administering to a viable cell containing targeted DNA a therapeutically effective amount of a photoactivatable composition comprising the UVA irradiation product of a compound that has two photoactivatable functional groups, and an oligonucleotide of DNA whose sequence of bases (a) contains at least one TA or AT sequence and (b) is substantially complementary to a segment of cellular DNA of the targeted DNA in the cell, and irradiating the cell with UVA light.

40 Claims, No Drawings

SELECTIVE INHIBITION OF GENE EXPRESSION BY PHOTOACTIVATABLE OLIGONUCLEOTIDES

CROSS REFERENCE TO RELATED APPLICATIONS

This application is a continuation-in-part application of copending U.S. application Ser. No. 299,265 filed Jan. 23, 1989, abandoned, which is a continuation-in-part of copending U.S. application Ser. No. 146,571 filed Jan. 21, 1988, abandoned.

BACKGROUND OF THE INVENTION

The present invention relates to photoactivatable therapeutic compounds and compositions, and methods of using said compounds and compositions to inhibit the function and/or expression of targeted DNA. More particularly, the invention disclosed herein relates to the therapeutic uses of photoactivatable therapeutic compositions comprising UVA (ultraviolet A light) irradiation products of nucleotide bases (the oligonucleotides) having predetermined sequences, and with compounds having two photoactivatable functional groups and which are reactable with at least one base of the oligonucleotides under UVA irradiation conditions.

Psoralen compounds are particularly useful as the difunctional compounds in the practice of this invention. The composition is administered to viable cells, preferably in vivo. The cells are thereafter exposed to UVA radiation. This results in inactivated or "turned-off" genes in the cell which have been targeted by the predetermined sequence of the oligonucleotide in the cells.

The oligonucleotide used to prepare the photoactivatable therapeutic material contains a base sequence segment that is complementary to a segment of the "sense" strand or a base sequence segment of the "antisense" DNA strand of a targeted gene. In the preparation of the photoactivatable therapeutic material, it is believed that the oligonucleotide reacts with a photoactivatable moiety of the difunctional compound upon UVA irradiation to form a monoadduct, and upon cellular administration and further UVA irradiation, the photoactivatable therapeutic composition crosslinks in situ to the complementary segment of DNA in the targeted gene.

Disclosed herein are photoactivatable therapeutic drugs which are believed to be chimeric molecules having a photoactivatable moiety and an oligonucleotide moiety, for example, photoactivatable psoralen monoadducts of oligonucleotides; methods for selectively inhibiting DNA function, for example, irradiating the psoralen-oligonucleotide monoadducts in viable cells with UVA; and methods for treating diseases comprising administration of the photoactivatable therapeutic materials of the present invention to targeted tissue, such as skin, followed by localized UVA irradiation of the site.

Phototherapeutic techniques have been known since biblical times. The Egyptians ingested the leaves of a weed (ammi majus) that grew by the Nile and then exposed themselves to sunlight to treat depigmented patches of skin (vitiligo). The active constituent of the ammi majus plant, isolated and characterized in 1947, is a derivative of psoralen, 8-methoxypsoralen (8-MOP). Lerner and associates, in 1953, established that purified 8-MOP could be administered safely to humans and photosensitized 8-MOP was efficacious at low doses in the management of vitiligo. The work by Lerner and associates created great interest and initiated the modern era of therapeutic photopharmacology, particularly in the field of dermatology. Subsequent research demonstrated that UVA irradiated psoralen derivatives (furocoumarins), such as 8-MOP, react with DNA. The therapeutic effects of photoactivated psoralens resulted from their photoreaction with bases in the two complementary strands of DNA.

Phototherapies that have been developed thus far using derivatives of psoralen, such as 8-MOP, have involved UVA light irradiation of skin after topical application or oral ingestion of the psoralen derivative and, more recently, extracorporeal irradiation of diseased blood.

Two of the earliest phototherapies were the treatment of vitiligo and psoriasis with psoralen and UVA. A more recent development has been the treatment of the leukemic phase of cutaneous T-cell lymphoma (CTCL) with psoralen and UVA. After oral administration of 8-MOP, a patient's blood is separated into three fractions by leukophoresis: erythrocytes, leukocytes and plasma. The leukocytes and plasma are combined and passed through a plastic cassette in which they are irradiated as a thin (1 mm) layer. "Treatment of Cutaneous T-Cell Lymphoma by Extracorporeal Photochemotherapy", Edelson, et al., Vol. 316, No. 6, *The New England Jour. Med.*, pp. 297–303, Feb. 5, 1987.

The psoralen derivative, 8-MOP (I), is a naturally occurring tricyclic aromatic compound whose planar structure facilitates intercalation between nucleic acid base pairs in DNA.

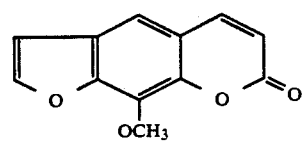

(I)

When activated with UVA light (320–400 nm), psoralens react with pyrimidine bases, preferentially with thymine, in cellular DNA. The preference for thymine over other nucleotide bases is about 20:1. Psoralens are polyfunctional reagents which form three distinct types of photoadducts with DNA: two monoaddition products and one cross-linked product. The monoadducts are either 3,4-"pyrone-side" cyclobutyl adducts of psoralen with the 5,6 carbons of thymine (such as illustrated for thymine above, II), or 4',5'-"furan-side" cyclobutyl adducts of psoralen with thymine (such as illustrated for thymine above, III).

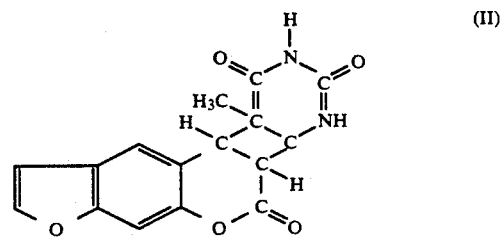

(II)

-continued

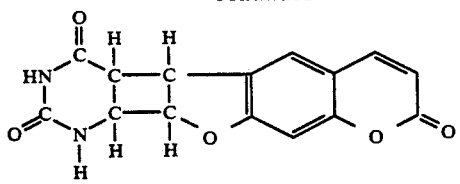
(III)

The 3,4-monoadduct of psoralen (II) has only a weak absorption band near 300 nm and therefore only weakly absorbs UVA light. The 4',5'-monoadduct of psoralen has an intense absorption band near 330 nm and thus is more readily capable of absorbing a second UVA photon. The second photon photoactivates the 3,4-pyrone ring leading to a second reaction with another thymine base (such as illustrated for thymine above, IV) on the opposite DNA strand thereby producing crosslinked DNA strands. In other words a psoralen acts to crosslink DNA strands by reacting with thymine bases in DNA strands. The 4',5'-monoadduct absorbs another UVA photon. Thus, crosslink formation of DNA is a two-photon process in which the absorption of the first photon leads to the formation of the 4',5'-monoadduct of psoralen to DNA, and the absorption of the second photon of UVA photoactivates the 3,4-pyrone ring of psoralen which subsequently adds to another thymine on the opposite DNA strand to give the crosslinked DNA.

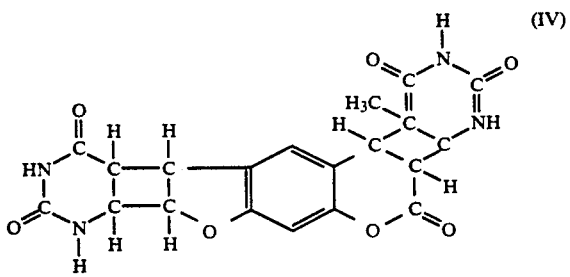
(IV)

Base pairing between complementary nucleic acid strands provides hydrophobic sites which are exquisitely suited for occupation by nonpolar psoralen molecules. Photoactivation of the bound and oriented psoralen moieties promotes the formation of psoralen photoadducts with pyrimidine bases (primarily thymine) in DNA. As noted above, possible reaction products include monoaddition adducts (monoadducts) and one diadduct or crosslink.

Several factors affect the photocondensation process. The ability of a particular psoralen to interact with DNA depends on its intrinsic thermodynamic properties which are related to the nature of the substituents on the core psoralen molecule. The psoralen partitions itself between the aqueous environment surrounding the DNA and the hydrophobic sites between base pairs. The distribution can be shifted towards more base pair intercalation by a) lowering the temperature, b) increasing the salt concentration of the reaction buffer, and c) altering substituents on the psoralen core (e.g., 4'-aminomethyl-4'5',8-trimethylpsoralen (AMT) in place of 8-MOP).

In the absence of base pairs the yield of psoralen photoadducts is reduced, and in the case of 8-MDP the yield is reduced by at least two orders of magnitude. Therefore base paired strands of DNA are used in the preferred method of producing the monoadducts of this invention.

To control the formation of monoadducts two strategies have been used. First, by irradiating psoralen-double stranded DNA solutions with wavelengths of UV light greater than 390 nm, monoadducts are virtually the only photoadducts formed. Second, by intentionally incorporating a mismatched base in the AT region of the oligonucleotide in the strand complementary to the target strand, monoadducts alone are produced regardless of which UVA wavelength is used for irradiation. For example, structure (V) represents a matched base pair, and structure (VI) represents a mismatched base pair wherein the mismatched complementary strand has an A in place of the complementary base T, thereby inhibiting psoralen from crosslinking between T bases in the mismatched strands.

| GAGTATGAG | (V) |
| CATAC | |
| GAGTATGAG | (VI) |
| CAAAC | |

By intentionally incorporating a mismatched base in the complementary strand, crosslink formation is blocked. Following irradiation, the mixture containing the monoadduct oligonucleotide is subject to denaturation to separate the unreacted complementary DNA strand from the oligonucleotide-psoralen monoadduct strand. Preliminary results indicate that monoadducts form with similar efficiencies when 8-MOP plus ds-DNA, either perfectly matched or containing a single mis-matched base, are irradiated with 400 nm light.

Phototherapies of the prior art involve the administration of a derivative of psoralen, for example 8-MOP, and subsequent UVA irradiation to produce monoadducts and crosslinks in complementary strands of DNA in irradiated cells that contain the 8-MOP. However, administration of a psoralen compound by itself is not specific for any particular locus of the DNA contained in the cells, and subsequent UVA irradiation causes the formation of monoadducts and crosslinks randomly throughout the cellular DNA.

One of the objects of the present invention is to target a particular nucleotide sequence in the cellular gene for photo-crosslinking with a monoadduct of a predetermined sequence of oligonucleotides and a compound that has at least two photoactivatable functional groups, which compound is reactable with at least one base of the oligonucleotide under UVA irradiation conditions. The result of such crosslinking reaction is that the gene containing the reaction product is turned off, i.e., the crosslinked DNA is inhibited from replicating and expressing the polypeptide for which it codes. Thus, at least one targeted segment of DNA of an entire genome is selectively modified by a crosslink in that gene, or some other DNA segment. Other genomic loci are therefore spared the effects of the photoactivated compound, such as psoralen. Oligomers complementary to a segment of one strand of DNA in the targeted gene, which are capable of locating and hybridizing with the targeted segment, were designed as the means of delivering photoactivatable compounds, such as the psoralen-oligonucleotide adduct, to a specific nucleotide sequence in the cellular gene prior to UVA irradiation and crosslink formation.

Although we do not wish to be bound by any theory by which inactivation of a targeted gene occurs, we believe that a photoactivated reaction occurs in vivo resulting in a gene or genes that are inactivated or "turned off". Thus, the therapeutic materials of this invention are referred to as photoactivatable because their therapeutic effects are initiated by UVA. It is believed that in the initial reaction, in vitro, a psoralen molecule conjugates to an oligonucleotide to form the 4',5'-monoadduct of the psoralen and the oligonucleotide.

The psoralen-oligonucleotide monoadducts of the present invention are administered to viable cells or tissue, such as by injection, or topical or intralesional application to the skin of animals, and are transported or otherwise caused to enter cells. We theorize that in the cell, the psoralen-oligonucleotide adduct hybridizes with the specific or complementary segment of DNA in the targeted DNA sequence. Subsequent in situ UVA irradiation of the hybridized photoactivatable psoralen-oligonucleotide material causes the psoralen-oligonucleotide material to react with or crosslink to the complementary strand to which it is hybridized and thereby inactivates the targeted DNA sequence.

Once the DNA sequence of a gene is known, or once the amino acid sequence of a polypeptide for which the gene codes are known, specific oligonucleotide sequences can be constructed by methods known in the art. The specific oligonucleotide sequence that is constructed should be complementary to at least a segment of DNA of the gene that is to be turned off. Therefore, any known gene locus containing a TA sequence or AT sequence would be a potential target for the phototherapeutic materials of this invention because the psoralen moiety of the monoadduct preferentially reacts with thymine bases, both in the oligonucleotide and in the cellular DNA.

The compositions of the present invention comprise photoactivatable oligonucleotides, e.g., the 4',5'-monoadducts of a psoralen compound, with specific, predetermined oligonucleotides that contain at least a TA or AT sequence and desirably a TAT or ATA sequence. These chimeric 4',5'-monoadduct compounds are believed to be formed after UVA irradiation of a mixture of a psoralen and a oligonucleotide of a predetermined sequence. The 4',5'-monoadduct of the psoralen may be separated from the reaction mixture that may contain other photoadducts produced by this first irradiation, as well as unreacted materials.

Other compounds containing at least two photoactivatable functional groups, which compounds are reactable with at least one base of the oligonucleotide under UVA irradiation conditions and therefore are usable in the therapeutic treatments described herein, include: N,N'-alkylene(C-1 to C-15)-bis-maleimides (e.g., N,N'-tetramethylene-bis-maleimide); N-H or N-alkyl(C-1 or C-8)-furanocarbostyrils (e.g., 7H-furano[3,2-g]quinolone-2); furanochromones (e.g., 7H-furano [3,2-g][1]benzopyran-5-one); and alkenyl(C-3 to C-10)oxycoumarins (e.g., 7-allyloxycoumarin).

The oligonucleotide moiety of the monoadduct is designed to hybridize to a segment of DNA of the targeted gene that contains a thymine base within the complementary sequence of the DNA. Thus, the useful irradiated product contains a psoralen 4',5'-monoadduct at a thymine site in the predetermined sequence of the oligonucleotide. The 4',5'-monoadduct is capable of hybridizing with and thereafter photoreacting with a complementary DNA sequence in a targeted gene.

Further, oligodeoxyribonucleotide- and oligodeoxyribonucleoside-alkylphosphonates complementary to selected sequences in targeted genes, are within the meaning of oligonucleotides or oligomers as used herein for the practice of the disclosed invention. Oligomers of oligodeoxyribonucleoside-lower(C-1 to C-3)alkylphosphonates are nonionic nucleic acid analogues that contain a neutral alkylphosphonate linkage that replaces the negatively charged phosphodiester internucleotide bond normally found in nucleic acids. The phosphonate linkage is resistant to hydrolysis by nucleases and therefore the nonionic oligonucleotides are able to penetrate cell walls. The invention contemplates that all or some of the internucleotide phosphates may be replaced with alkyl phosphonates. Selective replacement of the internucleotide phosphates with an alkyl (e.g., methyl) phosphonate to form a "hybrid" molecule has been found to be particularly advantageous in suppressing the activity of nucleolytic enzymes located in the skin toward these modified oligonucleotides. Significantly lesser concentration of oligonucleotide having a hybrid internucleotide linkage may be needed to achieve the same cellular effect as compared to completely substituted oligonucleotides.

The oligonucleotides used in this invention comprise predetermined sequences of DNA bases ranging in size from about 8 bases up to about 30 bases. Most preferably, the sequence is between about 12 and about 20 bases in length. Less than 8 bases in the sequence may be used as the predetermined sequence, however, the degree of uniqueness decreases rapidly with decreasing length thereby greatly reducing the potential specificity of the psoralen-oligonucleotide monoadduct for a targeted gene. In other words, the psoralen-oligonucleotide monoadduct may interact with other genes (genes not intended as the target gene) and cause undesirable inactivation of such other genes. On the other hand predetermined oligonucleotide sequences greater than about 30 bases may demand such a high degree of homology for recognition and hybridization of its complementary segment in the gene to be targeted, that it may prevent practical application of this invention. In other words, the time that may be required for hybridization of the longer predetermined oligonucleotide sequences to the complementary DNA segments of the targeted gene may render this process ineffective as a practical matter. Moreover, the transport across cell walls of 4',5'-psoralen-olignucleotide monoadducts having a long predetermined oligonucleotide sequence may be retarded or even inhibited.

With respect to the predetermined oligonucleotide sequence, the sequence must contain at least a thymine-adenine or adenine-thymine (TA or AT) dinucleotide sequence within the oligonucleotide. In other words, the predetermined sequence is selected from a complementary segment of DNA of the gene to be targeted that contains an AT or TA dinucleotide sequence. Preferably, the predetermined oligonucleotide sequence that is selected should contain multiple TA or AT sequences within the predetermined sequence. For example, TAT or ATA, and TATA or ATAT are preferred. It is also possible, but less desirable, for a cytosine to replace a thymine in the oligonucleotide or the target gene.

Accordingly, the predetermined sequence that is selected and has, for example 10 bases, may contain a TATA sequence and 6 additional bases. For example, in the gene for T3 (T cell receptor), the sequence 5'-GGAATATAGG-3' is found and it is appreciated that the selected sequence contains the desirable ATATA sequence. That 10 base sequence may be selected as the predetermined complimentary oligonucleotide sequence for use in this invention. In this example, the complementary oligonucleotide sequence normally is 5'-CCTATATTCC-3'.

The oligonucleotide sequence may be prepared by techniques well known in the art. For example, the oligonucleotide sequence may be prepared by solid phase synthesis in a DNA synthesizer, or less preferred, the complex technique of reverse transcriptase may be used.

In order to prepare the psoralen-oligonucleotide monoadduct, a buffered (pH 7.4) aqueous solution of psoralen, 0.05–0.2 mg/ml, is prepared. For each ml of psoralen solution there is added about 10–50 micrograms of the predetermined oligonucleotide at a concentration of about 0.01–0.05 mM. Thereafter the solution is irradiated with long wavelength UVA light (390–410 nm) from a monochromator for about 1–5 hours for each ml of psoralen-oligonucleotide solution. Larger solutions may be used if one irradiates for longer periods of time. In place of a UV lamp, one may use an incandescent or special fluorescent lamp. A UV lamp could be used together with a glass filter that eliminates the UVA wavelength that cause the crosslinking reaction, namely 320–370 nm.

The method of the present invention comprises administering to viable cells a therapeutically effective amount of the photoactivatable oligonucleotide, such as the 4',5'-psoralen-oligonucleotide monoadduct. Hybridization of the oligonucleotide moiety to its complementary DNA genetic locus in the cell is believed to occur and the cell is then irradiated with UVA light. The hybridized 4',5'-psoralen-oligonucleotide monoadduct crosslinks to the complementary DNA sequence within the targeted gene. Photoactivation of the 3,4-pyrone ring of the psoralen moiety of the psoralen-oligonucleotide monoadduct, and its subsequent addition to a thymine on the targeted DNA to which the oligonucleotide moiety of the monoadduct is hybridized, provides a diadduct crosslink thereby inhibiting the replication and expression of the genetic information in the targeted gene.

There are perhaps 1,000 diseases and disorders of the skin. The skin is the body's largest organ, amounting to 15 percent of the total body weight. Within each centimeter, there are about 100 sweat glands, four meters of nerves and more than 3,000 nerve cells responsive to touch, temperature, pressure and pain. It is also a vital part of the body's immune system; the highest concentration of lymphocytes involved in the body's defense mechanism is located in the skin. Further, epidermal cells are known to produce significant amounts of interleukin-1, interleukin-3, thymopoietin, interferon, granulocyte/monocyte colony stimulating factor, lymphocyte function-associated antigens (e.g., LFA-1) and intercellular adhesion molecules (e.g., ICAM-1). Inhibiting these genes or inhibiting other genes that encode proteins or peptides, such as CD1a, that participate in the immune reaction, from expressing such polypeptide products allows one to effectively treat a variety of serious or troublesome disorders of the immune system.

By examining the nucleotide sequence of any of the genes responsible for the production of the aforementioned polypeptides, or for any other targeted gene, one can select and prepare complementary oligonucleotides to specific AT or TA containing 8–30 base sequences within the targeted gene. The complementary sequences are used to prepare the compositions of the present invention. For example, the following sequences are complementary to sequences in the gene that encodes the intracellular adhesion molecule ICAM-1:

(1) TTT AGG CAA CGG GGT CTC TAT GCC CAA CAA CTT GGG CTG,
(2) CTC GCT CTG GTT CCC CAG TAT TAC TGC ACA CGT CAG CCG,
(3) CCG GGT CTG GTT CTT GTG TAT AAG CTG GCC GGC CAC CTC and
(4) GAG GCC TGC AGT GCC CAT TAT GAC TGC GGC TGC TAC CAC.

As it is most preferable that the oligonucleotide used in the compositions according to the invention contain an ATA or TAT sequence and be 12 to 20 nucleotide bases in length, several sequences included within each of the above sequences could be particularly suitable for producing a composition that inhibits expression of ICAM-1.

Similarly, the following sequences are complementary to sequences in the gene that encodes CD1a(T-6):

(1) TGT CAC CAA CCT CCA ACT TAT TCA CCT TCC CCT AAT TC,
(2) CA TAT C ATT TGC AGA TGT TAT TTC CTT CTC TCA GAA AAA,
(3) GAA GTA GCA AAA ACA GCA TAT CAT TTG CAG ATG TTA TTT,
(4) TGG AAT TGC TGT CCC AGG TAT GAG TCT GCA AAT CAC TCA,
(5) AAA TGA CCG AAT GGT GCG TAT ACG GAA TAA TGT TTC CAG,
(6) ACA GCC TCC TGT CAC CTG TAT CTC AAA AGG ATC TGG CCT,
(7) ATA TTC CCA GCC ACT GGA TAT GGC AAC CAT GAA TTG TTC,
(8) TGC AGA AAT GCT TGG CCA TAT TCC CAG CCA CTG GAT ATG,
(9) AAG AAG TAA XXX AGG CAC TAT CAC CGC CAA GAT GAT GAA,
(10) AAC TGC AAT TCA TCG GCG TAT CTA CGA ATT CCC TCA AAT,
(11) ACC TGT ATC TCA AAA GGA TAT TCA AAC TGC AAT TCA TGG,
(12) ACA GCC TCC TGT CAC CTG TAT CTC AAA AGG ATA TTC AAA,
(13) ATA TTC CCA GCC ACT GGA TAT GGC AAC CAT GAA TTG TTC, and
(14) ACT GAG AAG ATT GTG TGT TAT GTC ATT TTC ATG CTG ATT, wherein X=A,T,G or C.

Included within these sequences are 12 to 20 base sequences containing an AT or TA, and most preferably a TAT or ATA sequence that would be particularly useful in preparing compositions according to the present invention that could be used to block CD1a production.

Several sequences complementary to regions in the gene that encodes IL-6 receptor protein could be useful in blocking expression of the protein. These include the following:

(1) GGC GAC GCA CAT GGA CAC TAT GTA GAA AGA GCT GTC TCC,
(2) TTT GAC CGT TCA GCC CGA TAT CTG AGC TCA AAG CGT AGT, (3) GAA TAT TAT CAT CGT CTT TAT TAG TAG TAA GTG CCT GCA,
(4) AAT CTC TGA AGA GAA TAT TAT CAT CGT CTT TAT TAG TAG,
(5) TGG GGA AGA AGT AGT CTG TAT TGC TGA TGT CAT AAG GGC and
(6) TGG TGC CAC CCA GCC AGC TAT CTG GGG AAG AAC TAG TCT.

TA or AT-containing, or most preferably TAT-containing 12 to 20 base sequences that are included within these sequences can be used to produce compositions according to the invention for inhibiting expression of the IL-6 receptor protein.

Oligonucleotides complementary to regions in the gene that encodes GM-CSF include those having the following sequences:
(1) GAA AGC CTT GCA AGA GGC TAT AAG CAG CCC TGC AGG GCA,
(2) CTG CTA CAG AGG AAT GGA TAT AGA GAT CTT GAC TAC CCA,
(3) ATA CCC TCT GTG CCC CTG TAT AAT CAA TAC CTT CTC TCC,
(4) TTC TGT GTG GGG AAG CAC TAT TTC AAA AGC CCC TCT GTG,
(5) CCG TAG ACC CTG CTC GAA TAT CTT CAG GCG GGT CTG CAC,
(6) ACC GGA GTT GGG GGG CAG TAT GTC TGG TAG TAG CTG GCT,
(7) CTA GGG CTG AAT AGG AGC TAT GGC CTG TTC TTG GGG GGC, and
(8) CGT GGG GAA AGA ACT GTG TAT TTC TCT CGC TGC TGA G.

Photoactivatable compositions prepared using 12-20 base TA or AT-containing, and most preferably ATA or TAT-containing, oligonucleotides having sequences that are contained within these sequences can be used to inhibit expression of GM-CSF.

The following sequences are complementary to regions in the gene encoding IL-1α:
(1) ATG ATC CTC ATA AAG TTG TAT TTC ACA TTG CTC AGG AAG
(2) CTG ATC ATT GGC TCG AAT TAT ACT TTG ATT GAG GGG GTC
(3) ACC TGT GAT GGT TTT GGG TAT CTC AGG CAT CTC CTT CAG
(4) CTA CGC CTG GTT TTC CAG TAT CTG AAA GTC AGT GAT AGA AT or TA-containing, or preferably ATA or TAT-containing oligonucleotides having sequences contained within these sequences are useful in preparing compositions according to the present invention for inhibition of IL-1α expression.

The compositions and methods of the present invention are particularly suitable for treatment of skin disorders by local applications, such as topical application to skin or injection into the tissue to be treated with the photoactivatable therapeutic composition, because of the ease of subjecting epidermal cells to UVA irradiation. The photoactivatable therapeutic composition permeates the outer layer of the skin. Viable cells in the lower layer of the epidermis absorb the photoactivatable material into the cellular nuclei where the above referred to hybridization and subsequent UVA irradiation takes place.

Among the diseases which can be treated by the compositions of this invention are inflammatory diseases (such as atopic dermatis or lupus erythematosus), diseases of keratinization (such as ichthyosis or psoriasis), viral diseases (such as warts and herpes simplex), and neoplastic diseases (such as melanoma and cutaneous T cell lymphoma).

In addition, the photoactivatable oligonucleotide compositions and methods of the present invention can be effective in the selective inhibition of not only endogenous genes, but also exogenous genes, such as those derived from viral genomes present in skin cells or other targeted cells which are capable of being UVA irradiated.

The monoadducted oligonucleotides described herein may be formulated in suitable pharmaceutical vehicles for topical or intralesional administration for treatment of skin disorders, such as psoriasis. The instant compositions can be applied topically to or injected into the treatment site, e.g., subcutaneously by injection. When used for topical applications, the adduct is usually formulated with a pharmaceutically acceptable carrier.

Carrier materials are well known in the pharmaceutical formulation art and include those materials referred to as diluents or vehicles. The carrier may include inorganic or organic materials and should have sufficient viscosity to allow spreading of the composition and provide good adherence to the tissue to which it is topically applied. Examples of such carriers include, without limitation, polyols such as glycerol, propylene glycol, polyethylene glycol, suitable mixtures thereof, vegetable oils, and other materials well known to those skilled in this art. The viscosity of the formulation can be adjusted by methods well known in the art, for example, by the use of a higher molecular weight polyethylene glycols.

In addition to the adduct and carrier, the formulation may contain pharmacologically-acceptable additives or adjuvants such as antimicrobial agents, e.g., methyl, ethyl, propyl, and butyl esters of para-hydroxybenzoic acid, as well as chlorobutanol, phenol, ascorbic acid, etc. The formulation may also contain thickening or gelling agents, emulsifiers, wetting agents, coloring agents, buffers, stabilizers and preservatives including antioxidants such as butylhydroxyanisole in accordance with the practice of the art. The formulation may also contain penetration enhancers such as dimethyl sulfoxide, long-chain alcohols such as nonoxynol, long-chain carboxylic acids, propylene glycol, N-(2-hydroxyethyl)pyrrolidone,1-dodecyl-azacycloheptan-2-one, and the like. Depending on the method of application and specific therapeutic requirements, it may be desirable to use absorption-delaying agents such as aluminum monostearate and gelatin.

The composition of the formulation may be adjusted using components well-known in the formulation art to provide a pharmaceutical formulation which is a gel, cream, ointment, solid, liquid, semi-solid, etc. The particular physical form of the formulation depends on the desired method of treatment and the patient to be treated.

Typical formulations of the pharmaceutical compositions of this invention are set forth as follows:

| Application Form | Formulation | (Per 100 gms.) |
|---|---|---|
| Cream | Monoadducted Oligonucleotide | (preferred range 0.01–10%) |
| | Ascorbic acid | 0.1 |
| | Benzyl alcohol | 1 |
| | Propylene glycol | 15 |

| Application Form | Formulation | (Per 100 gms.) |
|---|---|---|
| | Water | 25 |
| | Stearyl alcohol | 6 |
| | Cetyl alcohol | 5 |
| | White petrolatum | 15 |
| | Poloxyl-40 stearate | 8 |
| Injectable Liquid | Monoadducted Oligonucleotide | (preferred range 0.01–10%) |
| | Water | 35 |
| | Glycerine | 5 |
| | Sodium chloride | 1 |
| | Sodium ascorbate | 0.1 |
| | Propylene glycol | 5 |

For administration by injection, the compositions according to the invention are formulated as solutions or suspensions having a low enough viscosity to be injected. The composition suitable for injectable use must be sterile and fluid to the extent that it allows easy injection. It should also be stable under conditions of manufacture and storage and be preserved against contamination by microorganisms. Preservatives include alcohol, benzoic acid, sorbic acid, and methyl and propyl paraben with and without propylene glycol. Additionally, the pH of the composition must be within the range which does not result in tissue damage or lead to chemical instability of the adduct, namely, between about 4–7.

The concentrations of active ingredients in a particular formulation required to provide a particular effective dose may be determined by a person skilled in the pharmaceutical formulation art based upon the properties of a carrier and the particular additives introduced into the formulation. Formulations may be prepared that have significantly higher concentrations of adduct depending upon the carrier and additives being used. If the carrier substantially retains the adduct or releases it at a slow rate, the concentrations of the adduct in the formulation can be substantially increased and in fact may have to be substantially increased in order to provide an effective treatment. In practice, it is preferred that a formulation contain the lowest concentrations of adduct which effectively treat the condition with the desired number of applications, i.e., a lower effective dose rate can be tolerated if multiple applications are used. This low concentration limit is dependent upon the delivery effectiveness of the carrier vehicle. Preferably, the adduct comprises between about 0.01 and about 10 weight percent of the formulation.

A preferred embodiment of the instant invention comprises formulations containing adduct, i.e., oligonucleotide 8MOP monoadduct. This formulation is particularly effective in treating psoriasis. Although the effective concentration of adduct delivered to the treatment site depends, inter alia, upon the carrier and other additives included in the formulation, ordinarily the concentration of adduct in the formulation ranges from about 0.01 to 10 weight percent. These ranges are provided by way of description and not by way of limitation since it is recognized that the concentration may be adjusted over a wide range depending on the carrier material, number of applications used, etc., as described hereinabove.

The pH of the formulation is important in assuring stability of the adduct as well as assuring that the formulation is physiologically acceptable to the patient. The pH of the formulation may be maintained through the use of toxicologically acceptable buffers. Such buffers are well known in the pharmaceutical formulation art, and include hydrochloric acid buffer, acid phthalate buffer, phosphate buffer and citric acid/sodium citrate buffer.

In topical applications the instant compositions are applied to the affected area or afflicted situs for the patient. The term "topical" refers herein to the surface of the epidermal tissue, especially the skin, and surface of psoriatic disease on the skin which have been modified, as well as sites from which plaques have been removed from the skin.

In preparing a formulation suitable for topical application, the adduct is normally mixed with a suitable solvent. Examples of solvents which are effective for this purpose include ethanol, acetone, acetic acid, aqueous alkaline solutions, dimethyl sulfoxide, glycerine, glycerol, propylene glycol, nonoxynol, ethyl ether, polyethylene glycol, etc.

Application by injection can be used for treatment of psoriasis. In this procedure the instant composition is injected directly into the psoriatically involved skin.

The following examples illustrate the principles and practices of the invention and are not intended to limit its scope in any way. All percentages are by weight unless otherwise indicated.

EXAMPLE 1

Preparation of a Photoactivatable Oligonucleotide Containing a 4',5' Monoadduct of 8-Methoxypsoralen Photoactivatable monoadducts of oligonucleotides containing a 4',5' monoadduct of 8-methoxypsoralen (8-MOP) were prepared, as follows. The sequences GAGTATGAG (complementary to a portion of the "sense" strand of a gene) and its complementary sequence, CATAC, were treated with 8-MOP and UVA light (320–400 nm) at 5° C. 8-MOP at 0.2 mg/ml (0.93 mM) oligomeric double helix consisting of equimolar amounts of the above 9-mer and 5-mer in a buffer (0.01M Tris, 0.001M EDTA and 0.5 NaCl, pH 7.4) were irradiated with 400 nm light using a grating monochromator. In this way the predominant photoadduct that was made was the 4',5'-monoadduct of the 9-mer. The 4',5' monoadducted oligonucleotide was separated from other oligonucleotide species denaturing using polyacrylamide gel electrophoresis (20% acrylamide with 8.3M urea). The gel bands were excised, soaked in distilled water to elute the oligonucleotide containing the monoadduct and then purified by cartridge chromatography. The purified 4',5'-8-MOP oligonucleotides are used to target 8-MOP to specific cellular DNA sequences.

A. Photochemistry: 8-MOP (0.2 mg/ml) and the [$^{32}$P]-oligonucleotide (0.03 mM) in Tris-EDTA buffer were irradiated with 400 nm light. In initial experiments the photochemical kinetics were determined by assaying the solution at 0, 0.5, 1, 2, and 3 hours in order to determine the optimum time for the production of the 4',5' monoadduct of 8-MOP to oligonucleotide.

B. Polyacrylamide Electrophoresis: Aliquots of the 8-MOP-oligonucleotide reaction mixture were mixed with a sucrose-dye mixture and applied to a polyacrylamide gel. The current was applied at 10–15 milliamps (about 1500–2000 volts) for about 5 hours. During electrophoresis the operative temperature of the gel was about 5° C.

C. Purification of 4',5' 8-MOP Oligomer: The [$^{32}$P]-oligonucleotide bands on the polyacrylamide gel were visualized by autoradiography. The autoradiogram was used as a template to excise the oligonucleotide bands from the gel. The excised gel band was soaked in distilled water for 4–8 hours to elute the 8-MOP-monoadducted oligonucleotide. The oligonucleotide solution (up to 10 ml containing 20–40 ug of oligonucleotide) was then applied to a Nensorb cartridge. After a wash to remove unretained species, the purified 8-MOP-oligonucleotide was eluted with a water:methanol solution (60%) at a flow rate of approximately 1 ml/minute. The 8-MOP-oligonucleotide was then lyophilized and dissolved in a small volume of distilled water and its concentration was determined by UV spectroscopy. By irradiating with shorter wavelength UVA light (320–370 nm), a solution containing the 8-MOP oligonucleotide in the presence of an oligonucleotide containing the complementary sequence, the ability of the monoadducted oligonucleotide to form crosslinks was verified. The yield of crosslinked oligonucleotides, which migrate more slowly than the original oligonucleotides was estimated by inspection of the autoradiogram.

EXAMPLE 2

Suppression of Ampicillin Resistance in *E. coli* by 8-MOP-Oligonucleotide

Ampicillin-resistant *E. coli* are rendered sensitive to ampicillin by treating the bacteria with an 8-MOP-oligonucleotide constructed by adducting an antisense oligomer of a portion of the ampicillin (amp) resistance gene with 8-MOP as described above in Example 1.

A. Bacteria and Media: *E. coli* strain XL-1 Blue from Stratagene, transformed with Bluescript plasmid, are resistant to ampicillin and tetracycline. The bacteria are grown in LB medium with tetracycline and with or without ampicillin.

B. 8-MOP-Oligonucleotide: The sequence 5'-CTCATACTC-3' occurs near the start of the amp resistance sequence (base numbers 2823–2832), and only in this site in the entire plasmid. The complementary sequence, 5'-GAGTATGAG-3', a nine-unit oligomer (or "9-mer"), is combined with 8-MOP and then purified as described above in Example 1. By recognizing its complementary sequence in the *E. coli* plasmid the 9-mer "positions" (or hybridizes) the 8-MOP monoadduct at a crosslinkable site. Crosslinking at this site by subsequent irradiation with UVA light (full spectrum) inhibits the production of "ampicillinase" and hence 8-MOP-oligomer treated bacteria survive in standard media, but not in media containing ampicillin. The specificity of this effect is demonstrated by showing that tetracycline resistance is not affected by this protocol.

The 9-mer complementary to the ampicillin sequence (2823–2832), modified as described above, is added to bacterial cultures and followed by irradiation with UVA light (1–2 Joules/cm$^2$). Controls include untreated bacteria as well as bacteria treated with either UVA alone or the 8-MOP-oligomer alone.

C. Protocol:

1. Initial Cultures: 50 ul of stationary phase bacteria containing the plasmid are innoculated into 5 ml cultures of LB media containing ampicillin (25 ug/ml) and 8-MOP-oligomer in the concentration range 0–1000 ng/ml (at a concentration of 0 ng/ml, it is a control) and are grown to stationary phase at 37° C.

2. Evaluation of 8-MOP-Oligomer Efficacy: Aliquots of confluent cultures are added (in groups of ten) to media containing either no antibiotic, ampicillin, tetracycline or ampicillin plus tetracycline. Five of the aliquots are treated with UVA light (irradiance 2.5 milliwatts/cm$^2$) for up to 15 minutes (1–2 J/cm$^2$). The other five aliquots in each group are kept in the dark. The cultures are grown with continuous shaking (220 rpm) at 37° C. until the group grown in the absence of any antibiotic is in the stationary phase. Viability is determined by plating the cultures on standard agar plates containing ampicillin and tetracycline. Established colonies are then counted within 7 days, and as soon as 1–2 days later.

3. Determination of Target Specificity: Another aliquot of the initial culture is irradiated as described above. The plasmid DNA is isolated and digested with the restriction enzymes, FnuH1 and NlaIV, yielding multiple fragments including one approximately 50 base pairs containing the target sequence. The digestion products are denatured and then electrophoresed. [$^{32}$P]-labeled fragment of the amp gene (containing the target sequence) is used as a probe in a Southern transfer analysis of the electrophoretically isolated DNA.

D. Results

1. Cultures treated with the 8-MOP-oligomer and UVA and grown in the presence of ampicillin have fewer colonies than any other group.

2. Probing the filter from the Southern transfer shows that the 50 base pair fragment of the plasmid isolated from the treated bacteria migrates at a different rate in comparison to DNA from untreated bacteria due to the crosslinking of the 8-MOP-oligomer in the former.

EXAMPLE III

Photoinactivation of Keratinocyte Cytokine Gene Expression

PAM 212 is a spontaneously transformed murine keratinocyte line derived from the skin of neonatal Balb/c mice. This homogeneous cell line constitutively produces IL-1 alpha and granulocyte macrophage colony stimulating factor (GM-CSF). The criteria by which this has been determined were: 1) Northern blot analysis using cDNA for murine macrophage IL-1 alpha and murine T cell GM-CSF; 2) biological activity in vitro assays using HT-2 cell proliferation for GM-CSF and D10.G4.1 cell co-stimulation for IL-1; and 3) characterization of purified, conditioned medium from PAM 212 cultures with antibodies raised to recombinantly-derived murine IL-1 alpha and GM-CSF.

PAM 212 cells are grown in Dulbecco's minimal essential medium (DMEM) supplemented with 10% fetal calf serum (FCS) as an adherent monolayer in tissue culture plastic. When the monolayer reaches confluence, cells cease to grow by contact inhibition. Confluent monolayers of PAM 212 cells can remain viable in a static growth phase for up to two months, with twice weekly medium changes. Cytokine production from such cultures remains constitutive. The protocol outlined below is designed to inhibit GM-CSF gene expression by the photoinactivation of the GM-CSF gene using an 8-MOP-modified antisense oligomer. The murine gene for GM-CSF contains the sequence 5'-CCCAGTACTC-3' which includes the major initiation site for GM-CSF in RNA synthesis. The psoralen target site in the complementary oligonucleotide strand is the complementary AT sequence. The control for specificity of this process is IL-1 gene expression in the same system.

A. Treatment of Cells: PAM 212 cells are grown in 75 cm² culture flasks until confluent cultures are obtained. After one week at confluence with medium changes every third day, the 8-MOP-oligomer (produced according to Example 1) is added to tissue culture media (concentration range: 0–100 ng/ml). After a 30 minute incubation with the PAM 212 cells, the cultures are treated with UVA light (1–2 J/cm²). The medium is decanted and the cultures are washed with three changes of PBS before fresh DMEM with 10% FCS is added again. Controls for the above manipulation include untreated cells, as well as cells treated with either UVA light or the 8-MOP-oligomer alone.

B. RNA Isolation: At 1, 2, 4, 8, 12, 16, 24, 36, 48, and 72 hours after the above treatment, the medium is harvested from the cells and frozen in 1 ml aliquots. Cells are collected and total cellular RNA is isolated by the guanidinium isothiocynate method of Chirgwin et al. Either total cellular RNA or poly A-selected RNA (enriched for messenger RNA, mRNA) is electrophoresed on an agarose gel and the gel blotted onto nylon filter membrane (zetabind). The membrane is hybridized with [$^{32}$P]-cDNA for GM-CSF and exposed to film at −70° C. Parallel experiments are run with [$^{32}$P]-cDNA for IL-1 alpha. Densitometry is used to assess quantitative differences in mRNA.

C. GM-CSF Activity: Medium is assayed for GM-CSF activity by incubation with HT-2 cells for 48 hours, followed by a 4 hour incubation with [$^{3}$H]-thymidine. Incorporation of thymidine into DNA is measured by scintillation spectrometry. The identity of the HT-2 stimulating factor is confirmed by parallel experiments in which neutralizing antibodies to GM-CSF are added to block its effect on the HT-2 cells. Analysis of proteins which are reactive with the anti-GM-CSF antibody is accomplished by an ELISA. Finally, freeze-thaw lysates of the cultured cells are tested for GM-CSF biological activity and protein in an identical fashion. Samples being tested for GM-SCF are also be tested for IL-1 using D10.G4.1 cloned T helper cells and concanavalin A. Samples are mixed with D10 cells in the presence of Con A and cultured for 72 hours, again followed by a 4 hour pulse with [$^{3}$H]-thymidine. Proliferation is measured by scintillation spectrometry.

D. Results

Successful and specific inhibition of GM-CSF gene expression yields the following results:

1. After 4 hours, GM-CSF mRNA is undetectable or markedly reduced by Northern blot analysis, but IL-1 alpha mRNA levels appear unchanged. Alternatively, a qualitatively (size) different GM-CSF mRNA accumulates as a result of aberrant and non-productive transcription of the altered GM-CSF gene.

2. No HT-2 stimulating activity is present in either conditioned medium or cell lysates of treated PAM 212 cells; this absence persists through the period of study. In contrast, the ability of conditioned medium and cell lysates to augment the proliferation of D10 cells in the presence of Con A is unaffected; that is, IL-1 activity is unaffected.

3. ELISA's reveal no immunoreactive GM-CSF in either conditioned medium or cell lysates of PAM 212 cells; in contrast IL-1 alpha immunoreactivity is unaffected. Alternatively, truncated non-functional GM-CSF peptides are evident in the conditioned medium and cell lysate.

EXAMPLE IV

A Phototherapeutic Cream Composition for the Treatment of Contact Dermatitis

A phototherapeutic cream composition for topical application to treat contact dermatitis in a subject patient comprises a phototherapeutic compound which is a chimeric molecule having a photoactivatable drug moiety and an oligonucleotide moiety, in combination with a pharmaceutical carrier therefor in the ratio of 0.01–10 parts by weight of photoactivatable therapeutic compound to 100 parts by weight of carrier. Preferably, the carrier should not absorb UVA light.

The photoactivatable therapeutic compound is a photoactivatable 4′,5′-monoadduct of 8-methoxypsoralen (8-MOP) and an oligonucleotide complementary to a segment of the DNA "sense" or "antisense" strand of the CD1 gene, synthesized and purified as described above in Example 1. The antisense oligonucleotide with which the 8-MOP has been photoreacted has the sequence 5′-TTCCTATAAGTT-3′. The psoralen in this antisense oligonucleotide is capable of reacting with thymine in the targeted gene sequence when it is exposed to UVA light.

The carrier formulation is adapted for application to skin and may facilitate the transportation of the photoactivatable therapeutic compound across the skin-cell membranes. Examples of suitable carrier formulations were described earlier herein.

A therapeutically effective amount of the phototherapeutic composition, about 0.5 parts by weight of the monoadduct, preferably in the cream formulation described in the above table, is applied to the skin of a subject patient, and after an effective amount of time, (approximately 30 minutes), the skin is irradiated with UVA light 1–5 J/cm² for 5–30 minutes. The DNA of the CD1 gene is thereby inhibited from functioning and the patient is relieved of the disease, contact dermatitis.

EXAMPLE V

Preparation of Oligonucleotides containing Hybrid Internucleotide Linkages for the anti-sense sequence 5′-GAGTATGAG-3′

Three oligonucleotides containing hybrid internucleotide groups having different methylphosphonate locations were prepared using commercially available reagents in a DNA synthesizer (Applied Biosystems). These hybrids were then complexed with a complimentary 5-base oligonucleotide, incubated with 4′-aminomethyl-4′5′,8-trimethylpsoralen (AMT), a psoralen derivative, and then irradiated with UVA. The oligonucleotides were then purified in accordance with Example I. Table I below sets forth the three hybrid oligonucleotides prepared and the location of their respective methylphosphonate groups.

The extent of specific photomodification of each of these hybrid molecules was determined by denaturing polyacrylamide gel electropheresis. The photochemical yield for each of these hybrid antisense oligonucleotides was similar to that observed in an unsubstituted unmodified control oligonucleotide.

TABLE I

| Hybrid | Location of Methylphosphonate (mp) |
| --- | --- |
| 9mer (alt-mp) | alternating, starting at position 2 |
| 9mer (TAT-mp) | TAT contained all methylphosphonates, the remainder unmodified |

TABLE I-continued

| Hybrid | Location of Methylphosphonate (mp) |
|---|---|
| 9mer (AG-mp) | Each AG pair (both 5' and 3' ends) |

EXAMPLE VI

Testing of Hybrid Oligonucleotides With Enzymes of Types Known To Occur in Human Skin An oligonucleotide (9mer), an ortho-phosphate (monoadduct) oligonucleotide (9mer-MA) and the three hybrid oligonucleotides prepared in Example V were exposed in appropriately buffered solutions to known epidermal type enzymes: T4 polymerase (T4 Pol), acid phosphatase (AP) and acid phosphatase/phosphodiesterase (AP/PDE). The sensitivities of the various oligonucleotides are set forth in Table II below.

TABLE II

| Oligonucleotide | T4 Pol | AP | AP/PDE |
|---|---|---|---|
| 9mer | 0 | 0 | 0 |
| 9mer (alt-mp) | ++ | ++ | ++ |
| 9mer(TAT-mp) | ++++ | +++ | ++ |
| 9mer(AG mp) | ++++ | ++ | +++ |
| 9mer (MA) | +++ | not tested | not tested |

(Scale: ++++ most resistant, 0 no resistance)

EXAMPLE VII

Sensitization of Normally Resistant Bacteria to Ampicillin

With reference to Example 2, *E. coli* containing a plasmid having the ampicillin resistance gene beta lactamase was treated with two concentrations of the monoadducted oligonucleotide (9mer-MA). The oligomer was introduced into the cells by the standard heat shock method. The cells were then incubated at 37° C. for 60 minutes to permit annealing of the oligomer (9mer) and then irradiated with UVA (2.3 mW/cm$^2$) for 30 minutes while on ice. Fresh media was added to the cells after UVA treatment and the cells were incubated for an additional hour. Cells (untreated controls and those treated with monoadducted 9mer [9mer-MA]) were plated on agar plates with and without ampicillin. Following an overnight incubation at 37° C., colony counts were performed. The ratio of colonies on plates with ampicillin compared to those without ampicillin were used to calculate the effect of 9mer-MA and UVA on colony growth as a measure of the suppression of ampicillin resistance of the *E. coli*.

Bacteria treated with 56 ng of 9mer-MA showed 29% growth inhibition while those treated with 112 ng showed 42% growth inhibition. Bacteria plated on tetracycline containing plates not containing ampicillin were not affected by the anti-sense oligonucleotide directed against the beta-lactamase enzyme sequence responsible for ampicillin resistance.

EXAMPLE VIII

S1 Nuclease Activity on Plasmid Strain SL-1 Blue Treated with Anti-sense Oligonucleotide A plasmid was obtained from *E. coli* (Strain XL-1 Blue) and an antisense oligonucleotide (9mer-MA) was synthesized using known reagents in a DNA synthesizer. The plasmid was denatured using 2M NaOH-2 mM EDTA and then incubated at 37° C. for 60 minutes with monoadducted oligonucleotide. This solution was exposed to UVA (320–400 nm, 2.8 mW/cm$^2$) for 30 minutes. The sample was then split into two fractions; one was denatured a second time with NaOH and EDTA. Each fraction was then incubated with S$_1$ nuclease (40 units in 33 nM NaOAc, 50 mM NaCl and 0.03 nM ZnSO$_{04}$) at 37° C. for 30 minutes and then immediately applied to a 20% polyacrylamide gel run under denaturing conditions.

The presence of a protected region was determined by denaturing polyacrylamide gel electrophoresis which showed a band corresponding to a protected region of double stranded oligonucleotide. This confirmed the existence of a double stranded configuration since the band could not have survived exposure to S1 nuclease otherwise.

Many obvious variations of the invention disclosed will suggest themselves to those skilled in the art. Nothing in the preceding specification is intended, however, to limit the scope of the invention as defined by the following claims.

What is claimed is:

1. A method of inhibiting the function of targeted DNA in a viable cell comprising:
   (a) administering to a viable cell containing targeted DNA a therapeutically effective amount of a photoactivatable composition comprising the UVA irradiation product of (a) a compound that has two photoactivatable functional groups, and (b) an oligonucleotide of DNA whose sequence of bases contains at least one TA or AT sequence and is substantially complementary to a segment of cellular DNA of said targeted DNA in said cell; and
   (b) irradiating said cell with UVA light.

2. The method of claim 1, wherein the difunctional compound is a psoralen compound.

3. The method of claim 2, wherein the difunctional compound is 8-methoxypsoralen.

4. The method according to claim 1 wherein the targeted DNA encodes a protein selected from the group consisting of interleukin-1, interleukin-3, IL-6 receptor, thymopoietin, interferon, granulocyte/-monocyte colony stimulating factor, lymphocyte function-associated antigen, intercellular adhesion molecules and CD1a.

5. The method according to claim 4 wherein the lymphocyte function-associated antigen is LFA-1 and the intercellular adhesion molecule is ICAM-1.

6. The method of claim 1 wherein the targeted DNA is a bacterial antibiotic resistance sequence.

7. The method of claim 6 wherein the targeted DNA in an ampicillin resistance sequence.

8. The method of claim 7 wherein the sequence of the oligonucleotide comprises GAGTATGAG.

9. A photoactivatable therapeutic composition for inhibiting the function of targeted DNA in a viable cell comprising the UVA irradiation product of (a) a compound that has two photoactivatable functional groups, and (b) an oligonucleotide of DNA whose sequence of bases contains at least one TA or AT sequence and is substantially complementary to a segment of cellular DNA of said targeted DNA in said cell, said UVA irradiation product being capable of reacting with said targeted DNA in said cell under photoactivatable conditions to inhibit functioning of said cell, and a pharmaceutically acceptable carrier for said UVA irradiation product in the ratio of 0.01–20 parts by weight of said product to 100 parts by weight of carrier.

10. The photoactivatable therapeutic composition of claim 9, wherein the difunctional compound is a psoralen compound.

11. The composition according to claim 9 wherein the targeted DNA encodes a protein selected from the group consisting of interleukin-1, interleukin-3, IL-6 receptor, thymopoietin, interferon, granulocyte-/monocyte colony stimulating factor, lymphocyte function-associated antigens, intercellular adhesion molecules and CD1a.

12. The composition according to claim 11 wherein the lymphocyte function-associated antigen is LFA-1.

13. The composition according to claim 11 wherein the intracellular adhesion molecule is ICAM-1.

14. The composition according to claim 13 wherein said complementary DNA is an AT or TA-containing 12 to 20 base oligonucleotide.

15. The composition according to claim 14, wherein the sequence of said 12 to 20 bases is a sequence contained within one of the following sequences:
(1) TTT AGG CAA CGG GGT CTC TAT GCC CAA CAA CTT GGG CTG,
(2) CTC GCT CTG GTT CCC CAG TAT TAC TGC ACA CGT CAG CCG,
(3) CCG GGT CTG GTT CTT GTG TAT AAG CTG GCC GGC CAC CTC and
(4) GAG GCC TGC AGT GCC CAT TAT GAC TGC GGC TGC TAC CAC.

16. The composition according to claim 15 wherein the difunctional compound is a psoralen compound.

17. The composition according to claim 16 wherein the difunctional compound is 8-methoxypsoralen.

18. The composition according to claim 11 wherein said targeted DNA encodes the protein CD1a.

19. The composition according to claim 18 wherein said complementary DNA is an AT or TA-containing 12 to 20 base oligonucleotide.

20. The composition according to claim 19, wherein the sequence of said 12 to 20 bases is a sequence contained within one of the following sequences:
(1) TGT CAC CAA CCT CCA ACT TAT TCA CCT TCC CCT AAT TC,
(2) CA TAT C ATT TGC AGA TGT TAT TTC CTT CTC TCA GAA AAA,
(3) GAA GTA GCA AAA ACA GCA TAT CAT TTG CAG ATG TTA TTT,
(4) TGG AAT TGC TGT CCC AGG TAT GAG TCT GCA AAT CAC TCA,
(5) AAA TGA CCG AAT GGT GCT TAT ACG GAA TAA TGT TTC CAG,
(6) ACA GCC TCC TGT CAC CTG TAT CTC AAA AGG ATC TGG CCT,
(7) ATA TTC CCA GCC ACT GGA TAT GGC AAC CAT GAA TTG TTC,
(8) TGC AGA AAT GCT TGG CCA TAT TCC CAG CCA CTG GAT ATG,
(9) AAG AAG TAA XXX AGG CAC TAT CAC CGC CAA GAT GAT GAA,
(10) AAC TGC AAT TCA TCG GCG TAT CTA CGA ATT CCC TCA AAT,
(11) ACC TGT ATC TCA AAA GGA TAT TCA AAC TGC AAT TCA TGG,
(12) ACA GCC TCC TGT CAC CTG TAT CTC AAA AGG ATA TTC AAA,
(13) ATA TTC CCA GCC ACT GGA TAT GGC AAC CAT GAA TTG TTC, and
(14) ACT GAG AAG ATT GTG TGT TAT GTC ATT TTC ATG CTG ATT, wherein X=A,T,G or C.

21. The composition according to claim 20 wherein the difunctional compound is a psoralen compound.

22. The composition according to claim 21 wherein the difunctional compound is 8-methoxypsoralen.

23. The composition according to claim 11 wherein said targeted DNA encodes the IL-6 receptor protein.

24. The composition according to claim 23 wherein said complementary DNA is an AT or TA-containing 12 to 20 base oligonucleotide.

25. The composition according to claim 24 wherein the sequence of said 12 to 20 bases is a sequence contained within one of the following sequences:
(1) GGC GAC GCA CAT GGA CAC TAT GTA GAA AGA GCT GTC TCC,
(2) TTT GAC CGT TCA GCC CGA TAT CTG AGC TCA AAG CGT AGT,
(3) GAA TAT TAT CAT CGT CTT TAT TAG TAG TAA GTG CCT GCA,
(4) AAT CTC TGA AGA GAA TAT TAT CAT CGT CTT TAT TAG TAG,
(5) TGG GGA AGA AGT AGT CTG TAT TGC TGA TGT CAT AAG GGC and
(6) TGG TGC CAC CCA GCC AGC TAT CTG GGG AAG AAC TAG TCT.

26. The composition according to claim 25 wherein the difunctional compound is a psoralen compound.

27. The composition according to claim 26 wherein the difunctional compound is 8-methoxypsoralen.

28. The composition according to claim 11 wherein said targeted DNA encodes the protein GM-CSF.

29. The composition according to claim 20 wherein said complementary DNA is an AT or TA-containing 12 to 20 base oligonucleotide.

30. The composition according to claim 29 wherein the sequence of said 12 to 20 bases is a sequence contained within one of the following sequences:
(1) GAA AGC CTT GCA AGA GGC TAT AAG CAG CCC TGC AGG GCA,
(2) CTG CTA CAG AGG AAT GGA TAT AGA GAT CTT GAC TAC CCA,
(3) ATA CCC TCT GTG CCC CTG TAT AAT CAA TAC CTT CTC TCC,
(4) TTC TGT GTG GGG AAG CAC TAT TTC AAA AGC CCC TCT GTG,
(5) CCG TAG ACC CTG CTC GAA TAT CTT CAG GCG GGT CTG CAC,
(6) ACC GGA GTT GGG GGG CAG TAT GTC TGG TAG TAG CTG GCT,
(7) CTA GGG CTG AAT AGG AGC TAT GGC CTG TTC TTG GGG GGC, and
(8) CGT GGG GAA AGA ACT GTG TAT TTC TCT CTC GCT GCT GAG.

31. The composition according to claim 30 wherein the difunctional compound is a psoralen compound.

32. The composition according to claim 31 wherein the difunction compound is 8-methoxypsoralen.

33. The composition according to claim 11 wherein said targeted DNA is IL-1α.

34. The composition according to claim 33 wherein said complementary DNA is an AT or TA-containing 12 to 20 base oligonucleotide.

35. The composition according to claim 34 wherein the sequence of said 12 to 20 bases is a sequence contained within one of the following sequences:
(1) ATG ATC CTC ATA AAG TTG TAT TTC ACA TTG CTC AGG AAG (2) CTG ATC ATT GGC TCG AAT TAT ACT TTG ATT GAG GGG GTC
(3) ACC TGT GAT GGT TTT GGG TAT CTC AGG CAT CTC CTT CAG
(4) CTA CGC CTG GTT TTC CAG TAT CTG AAA GTC AGT GAT AGA.

36. The composition according to claim 35 wherein the difunctional compound is a psoralen compound.

37. The composition according to claim 36 wherein the difunctional compound is 8-methoxypsoralen.

38. The composition of claim 9 wherein the targeted DNA is a bacterial antibiotic resistance sequence.

39. The method of claim 38 wherein the targeted DNA in an ampicillin resistance sequence.

40. The method of claim 39 wherein the sequence of the oligonucleotide comprises GAGTATGAG.

* * * * *